United States Patent [19]
Ogle et al.

[11] Patent Number: 5,817,024
[45] Date of Patent: Oct. 6, 1998

[54] HAND HELD ULTRASONIC DIAGNOSTIC INSTRUMENT WITH DIGITAL BEAMFORMER

[75] Inventors: William R. Ogle, Bothell; Larry Greisel, Seattle; Blake W. Little, Bothell; Justin Coughlin, Seattle; Steven G. Danielson, Seattle; Lauren S. Pflugrath, Seattle, all of Wash.

[73] Assignee: SonoSight, Inc., Bothell, Wash.

[21] Appl. No.: 863,937

[22] Filed: May 27, 1997

Related U.S. Application Data

[63] Continuation-in-part of Ser. No. 672,782, Jun. 28, 1996, Pat. No. 5,722,412.

[51] Int. Cl.$^6$ ...................................................... A61B 8/00
[52] U.S. Cl. ............................................................ 600/447
[58] Field of Search ................................... 600/444, 445, 600/446, 447, 459; 73/625, 626, 628, 633, 640, 641, 642

[56] References Cited

U.S. PATENT DOCUMENTS

| | | | |
|---|---|---|---|
| 4,173,007 | 10/1979 | McKeighen et al. ...................... | 367/11 |
| 5,123,415 | 6/1992 | Daigle ................................. | 128/661.01 |
| 5,295,485 | 3/1994 | Shinomura et al. ............... | 128/660.07 |
| 5,360,005 | 11/1994 | Wilk ..................................... | 128/653.1 |
| 5,369,624 | 11/1994 | Fukukita et al. ........................ | 600/447 |
| 5,590,658 | 1/1997 | Chiang et al. ..................... | 128/661.01 |
| 5,690,114 | 11/1997 | Chiang et al. .......................... | 600/447 |
| 5,709,209 | 1/1998 | Friemel et al. ......................... | 600/447 |

OTHER PUBLICATIONS

Minivisor Service Manual from Organon Teknika (Sep. 1979).

Ultra PCI System Specifications from Advanced Medical Products of Columbia, South Carolina (date unknown).

"Micros Q.V." brochure by Advanced Medical Products, Inc. (Sep. 1996).

*Primary Examiner*—George Manuel
*Attorney, Agent, or Firm*—W. Brinton Yorks, Jr.

[57] ABSTRACT

A hand held ultrasonic instrument is provided in a portable unit which performs both B mode and Doppler imaging. The instrument includes a transducer array mounted in a hand-held enclosure, with an integrated circuit transceiver connected to the elements of the array for the reception of echo signals. A digital beamformer is located in the hand-held enclosure for forming ultrasonic scanlines from the echo signals received by the elements of the array.

28 Claims, 15 Drawing Sheets

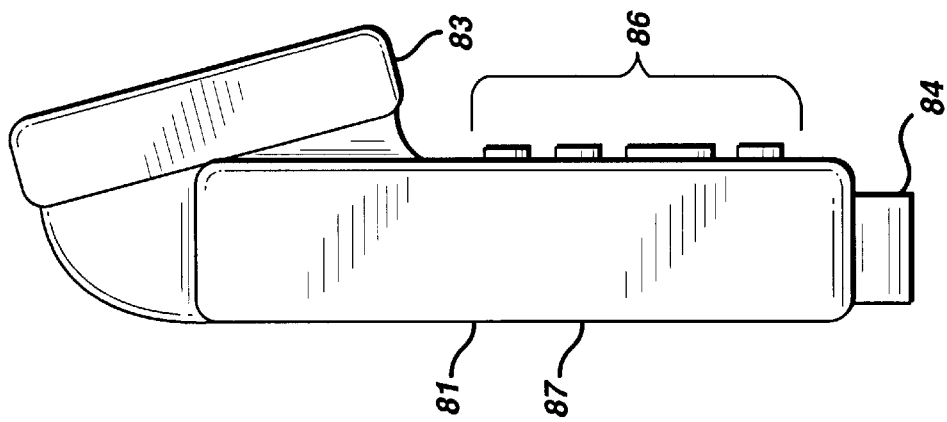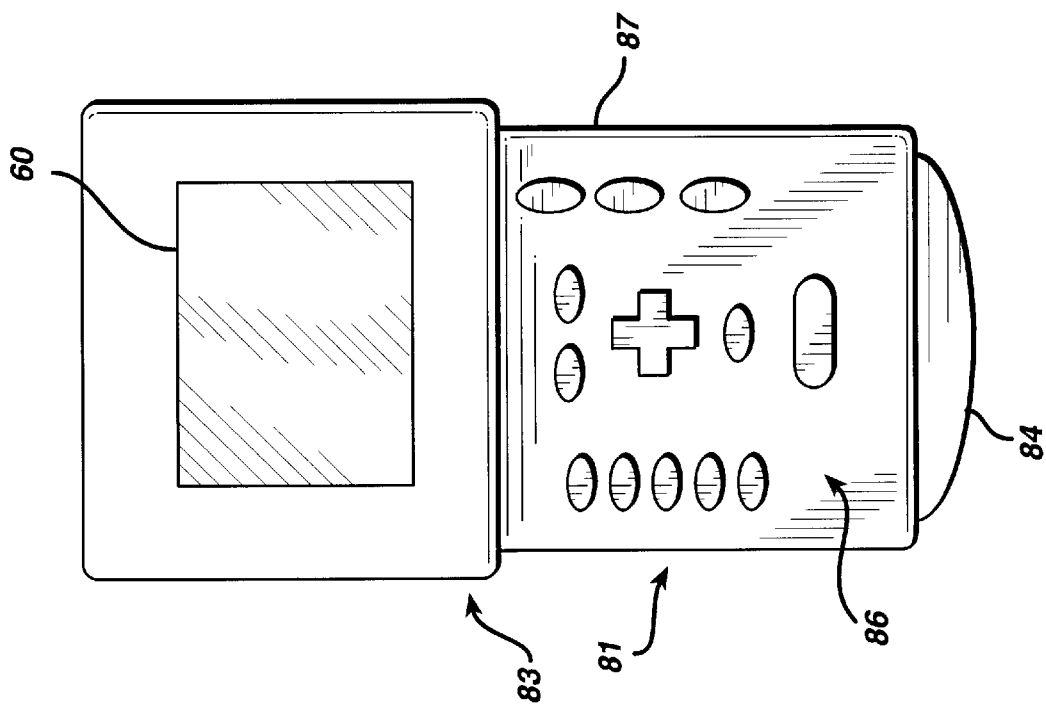

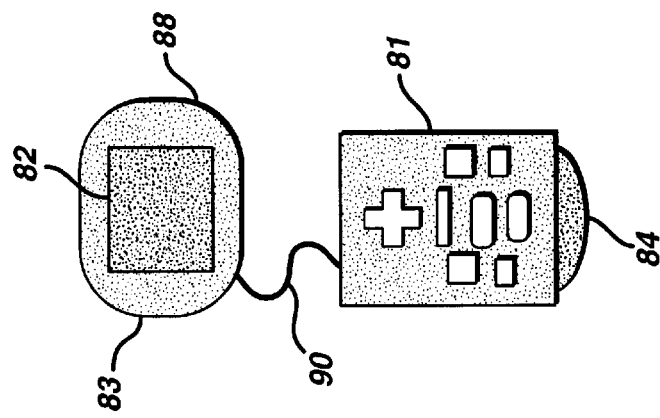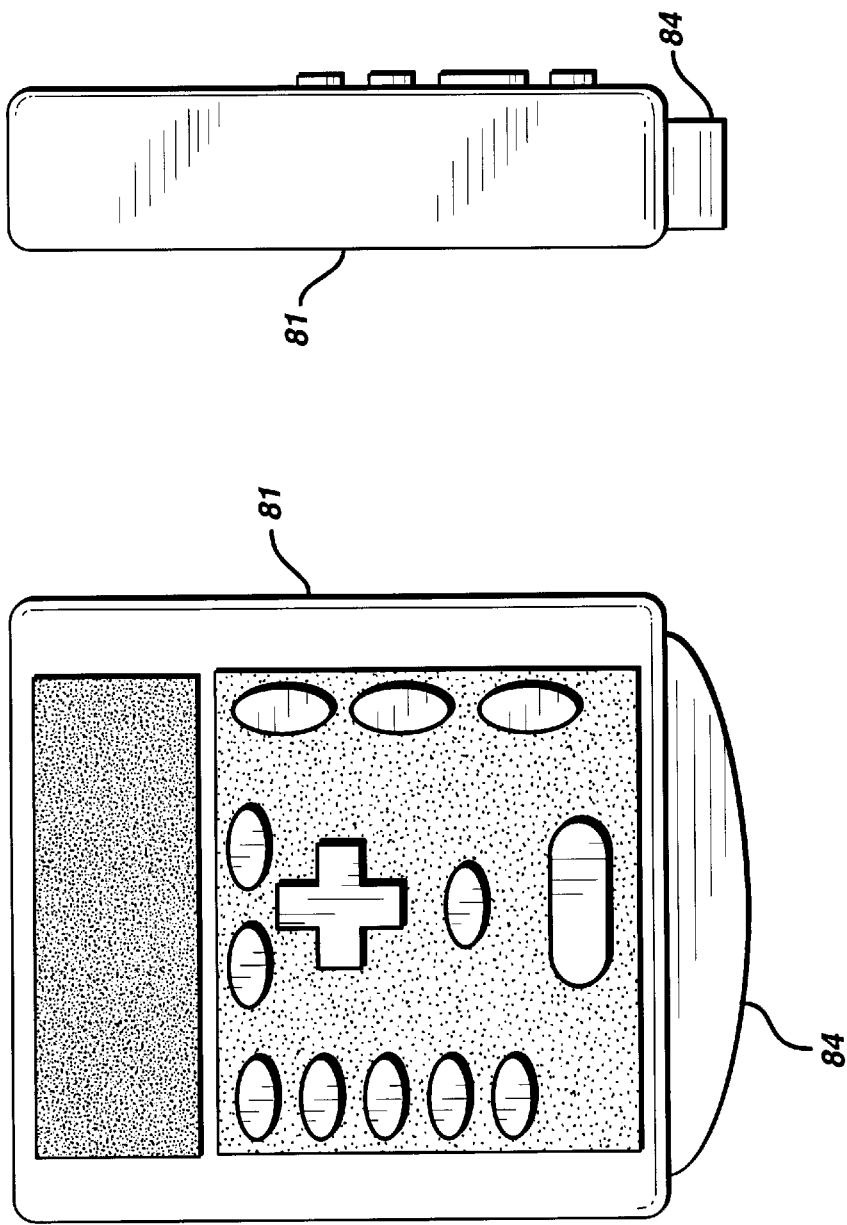

FIG. 16

| SWITCH FUNCTION | | DESCRIPTION | NUMBER OF CONTACTS |
|---|---|---|---|
| POWER OFF/ON | ⬯ | SLIDE SWITCH | 1 |
| ACTIVE SCAN/FREEZE | ◯ | PUSH AND HOLD FOR ACTIVE SCAN | 1 |
| CPA | ◯ | ENABLES AND DISABLES COLOR POWER ANGIO CPA | 1 |
| DOPPLER/CPA FILTER | ◯ | HIGH/MEDIUM/LOW BUTTON CYCLES THROUGH 3 SELECTIONS | 1 |
| 3D IMAGING MODE | ◯ | ENABLES 3D CAPTURE WHEN ENGAGED BEFORE THE ACTIVE SCAN BUTTON IS PUSHED | 1 |
| PRINT | ◯ | SENDS SERIAL SIGNAL TO PRINTER | 1 |
| CURSOR POSITION | ✦ | X/Y POSITION OF CURSOR | 4 |
| ENTER | ◯ | ENTERS SELECTION | 1 |
| MENU | ◯ | TOGGLES MENU FUNCTIONS OFF AND ON, USES CURSOR AND ENTER. FUNCTIONS: APPLICATION SELECTION USED TO ENTER ALPHA NUMERIC DATA, PATIENT ID, PATIENT NAME, CINE 2D AND 3D REVIEW | 1 |
| MEASURE | ◯ | ENABLES MEASUREMENTS, USES CURSOR AND ENTER | 1 |
| FOCUS | ◯ | ENABLES FOCUS MODE, CURSOR UP DOWN POSITIONS FOCUS, CURSOR LEFT RIGHT SELECTS NUMBER OF ZONES | 1 |
| IMAGE | ◯◯ | ALLOWS THE USER TO SELECT THROUGH SEVERAL GRAY SCALE CURVES, SPATIAL AND TEMPORAL FILTERS WITHIN A PREDETERMINED SET OF SETUPS FOR A SELECTED APPLICATION | 2 |
| DEPTH | ◯◯ | UP/DOWN, 5 DEPTH SELECTIONS | 2 |
| TGC GAIN | ◯◯ | UP/DOWN | 2 |
| BRIGHTNESS | ◯◯ | LCD DISPLAY CONTROL UP/DOWN | 2 |
| CONTRAST | ◯◯ | LCD DISPLAY CONTROL UP/DOWN | 2 |

HAND HELD ULTRASONIC DIAGNOSTIC INSTRUMENT WITH DIGITAL BEAMFORMER

This is a continuation-in-part of U.S. patent application Ser. No. 08/672,782, filed Jun. 28, 1996 now U.S. Pat. No. 5,722,412.

This invention was made with government support under agreement no. N00014-96-2-0002 awarded by the Office of Naval Research. The government has certain rights in the invention.

This invention relates to medical ultrasonic diagnostic systems and, in particular, to a fully integrated hand held ultrasonic diagnostic instrument.

As is well known, modern ultrasonic diagnostic systems are large, complex instruments. Today's premium ultrasound systems, while mounted in carts for portability, continue to weigh several hundred pounds. In the past, ultrasound systems such as the ADR 4000 ultrasound system produced by Advanced Technology Laboratories, Inc., assignee of the present invention, were smaller, desktop units about the size of a personal computer. However, such instruments lacked many of the advanced features of today's premium ultrasound systems such as color Doppler imaging and three dimensional display capabilities. As ultrasound systems have become more sophisticated they have also become bulkier.

However, with the ever increasing density of digital electronics, it is now possible to foresee a time when ultrasound systems will be able to be miniaturized to a size even smaller than their much earlier ancestors. The physician is accustomed to working with a hand held ultrasonic scanhead which is about the size of an electric razor. It would be desirable, consistent with the familiar scanhead, to be able to compact the entire ultrasound system into a scanhead-sized unit. It would be further desirable for such an ultrasound instrument to retain as many of the features of today's sophisticated ultrasound systems as possible, such as speckle reduction, color Doppler and three dimensional imaging capabilities.

In accordance with the principles of the present invention, a diagnostic ultrasound instrument is provided which exhibits many of the features of a premium ultrasound system in a hand held unit. The instrument can be produced as a single unit or, in a preferred embodiment, the instrument is a two-part unit, one including a transducer, beamformer, and image processor and the other including a display and power source for both units. In such a configuration the transducer/processor unit can be manipulated with one hand while a cable between the two units enables the video to be shown on the display unit while the latter unit is held or positioned for optimal viewing of the ultrasound image. The cable also provides energy for the transducer/processor unit from the display unit.

In a preferred embodiment the ultrasound system, from the transducer through to a video output, is fabricated on four types of application specific integrated circuits (ASICs): a transmit/receive ASIC which is connected to the elements of an array transducer, a front end ASIC which performs and controls transmit and receive beamforming with a plurality of delay channels, a digital signal processing ASIC which provides processing of the ultrasound signals such as filtering, and a back end ASIC which receives processed ultrasound signals and produces ultrasound image data. The image can be displayed on either a standard monitor or on a liquid crystal display (LCD). Comprised as it is of ASICs, the electronics of the unit can be fabricated on a single printed circuit board, eliminating the problems conventionally posed by connectors and cables. This sophisticated ultrasound instrument can be manufactured as a hand held unit weighing less than five pounds.

In the drawings:

FIGS. 2a and 2b are front and side views of a hand-held ultrasound system of the present invention which is packaged as a single unit;

FIGS. 3a and 3b are front and side views of the transducer unit of a two-unit hand-held ultrasound system of the present invention;

FIG. 4 illustrates the two units of a hand-held ultrasound system of the present invention in a two-unit package;

FIG. 16 is a chart of the user controls of the ultrasound system of FIG. 1.

Figure 1:
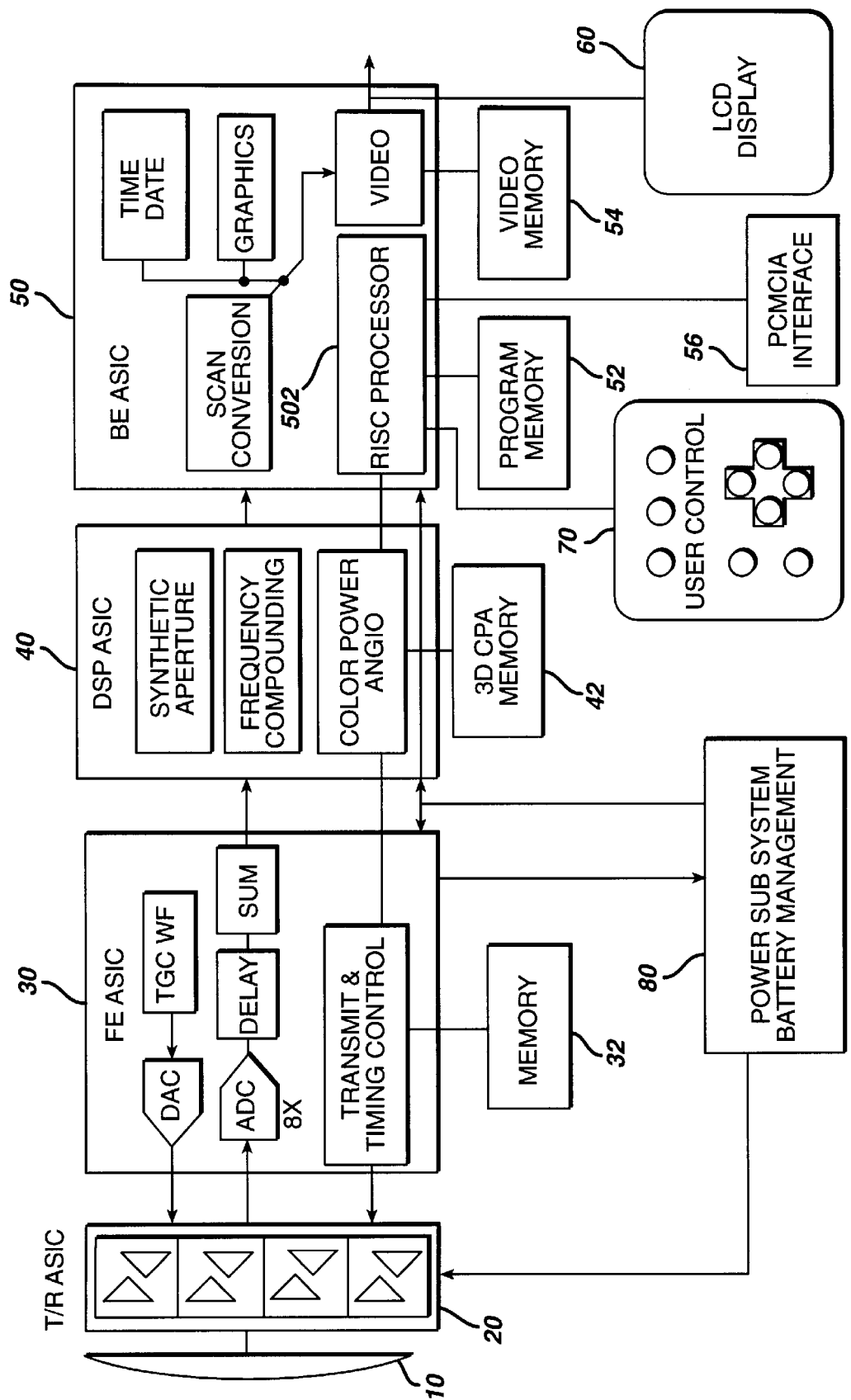
FIG. 1 illustrates in block diagram form the architecture of a hand-held ultrasound system of the present invention.

Referring first to FIG. 1, the architecture of a hand-held ultrasound system of the present invention is shown. It is possible to package an entire ultrasound system in a single hand-held unit only through judicious selection of functions and features and efficient use of integrated circuit and ultrasound technology. A transducer array 10 is used for its solid state, electronic control capabilities, variable aperture, image performance and reliability. Either a flat or curved linear array can be used. In a preferred embodiment the array is a curved array, which affords a broad sector scanning field. While the preferred embodiment provides sufficient delay capability to both steer and focus a flat array such as a phased array, the geometric curvature of the curved array reduces the steering delay requirements on the beamformer. The elements of the array are connected to a transmit/receive ASIC 20 which drives the transducer elements and receives echoes received by the elements. The transmit/receive ASIC 30 also controls the active transmit and receive apertures of the array 10 and the gain of the received echo signals. The transmit/receive ASIC is preferably located within inches of the transducer elements, preferably in the same enclosure, and just behind the transducer.

Echoes received by the transmit/receive ASIC 20 are provided to the adjacent front end ASIC 30, which digitizes and beamforms the echoes from the individual transducer elements into coherent scanline signals. The front end ASIC 30 also controls the transmit waveform timing, aperture and focusing of the ultrasound beam through control signals provided for the transmit/receive ASIC. In the illustrated embodiment the front end ASIC 30 provides timing signals for the other ASICs and time gain control. A power and battery management subsystem 80 monitors and controls the power applied to the transducer array, thereby controlling the acoustic energy which is applied to the patient and minimizing power consumption of the unit. A memory device 32 is connected to the front end ASIC 30, which stores data used by the beamformer.

Beamformed scanline signals are coupled from the front end ASIC 30 to the adjacent digital signal processing ASIC 40. The digital signal processing ASIC 40 filters the scanline signals and in the preferred embodiment also provides several advanced features including synthetic aperture formation, frequency compounding, Doppler processing such as power Doppler (color power angio) processing, and speckle reduction.

The ultrasound B mode and Doppler information is then coupled to the adjacent back end ASIC 50 for scan conversion and the production of video output signals. A memory device 42 is coupled to the back end ASIC 50 to provide storage used in three dimensional power Doppler (3D CPA) imaging. The back end ASIC also adds alphanumeric information to the display such as the time, date, and patient identification. A graphics processor overlays the ultrasound image with information such as depth and focus markers and cursors. Frames of ultrasonic images are stored in a video memory 54 coupled to the back end ASIC 50, enabling them to be recalled and replayed in a live Cineloop® realtime sequence. Video information is available at a video output in several formats, including NTSC and PAL television formats and RGB drive signals for an LCD display 60 or a video monitor.

The back end ASIC 50 also includes the central processor for the ultrasound system, a RISC (reduced instruction set controller) processor 502. The RISC processor is coupled to the front end and digital signal processing ASICs to control and synchronize the processing and control functions throughout the hand-held unit. A program memory 52 is coupled to the back end ASIC 50 to store program data which is used by the RISC processor to operate and control the unit. The back end ASIC 50 is also coupled to a data port configured as an infrared transmitter or a PCMCIA interface 56. This interface allows other modules and functions to be attached to or communicate with the hand-held ultrasound unit. The interface 56 can connect to a modem or communications link to transmit and receive ultrasound information from remote locations. The interface can accept other data storage devices to add new functionality to the unit, such as an ultrasound information analysis package.

The RISC processor is also coupled to the user controls 70 of the unit to accept user inputs to direct and control the operations of the hand-held ultrasound system.

Power for the hand-held ultrasound system in a preferred embodiment is provided by a rechargeable battery or an a.c. adapter. Battery power is conserved and applied to the components of the unit from the power subsystem 80. The power subsystem 80 includes a DC converter to convert the low battery voltage to a higher voltage which is applied to the transmit/receive ASIC 20 to drive the elements of the transducer array 10.

FIGS. 2a and 2b illustrate a one piece unit 87 for housing the ultrasound system of FIG. 1. The front of the unit is shown in FIG. 2a, including an upper section 83 which includes the LCD display 60. The lower section 81 includes the user controls as indicated at 86. The user controls enable the user to turn the unit on and off, select operating characteristics such as the mode (B mode or Doppler), color Doppler sector or frame rate, and special functions such as three dimensional display. The user controls also enable entry of time, date, and patient data. A four way control, shown as a cross, operates as a joystick to maneuver cursors on the screen or select functions from a user menu. Alternatively a mouse ball or track pad can be used to provide cursor and other controls in multiple directions. Several buttons and switches of the controls are dedicated for specific functions such as freezing an image and storing and replaying an image sequence from the Cineloop memory.

At the bottom of the unit 87 is the aperture 84 of the curved transducer array 10. In use, the transducer aperture is held against the patient to scan the patient and the ultrasound image is displayed on the LCD display 60.

FIG. 2b is a side view of the unit 87, showing the depth of the unit. The unit is approximately 20.3 cm high, 11.4 cm wide, and 4.5 cm deep. This unit contains all of the elements of a fully operational ultrasound system with a curved array transducer probe, in a single package weighing less than five pounds. A major portion of this weight is attributable to the battery housed inside the unit.

FIGS. 3 and 4 illustrate a second packaging configuration in which the ultrasound system is housed in two separate sections. A lower section 81 includes the transducer array, the electronics through to a video signal output, and the user controls. This lower section is shown in FIG. 3a, with the curved transducer array aperture visible at the bottom. The lower section is shown in the side view of FIG. 3b. This lower section measures about 11.4 cm high by 9.8 cm wide by 2.5 cm deep. This unit has approximately the same weight as a conventional ultrasound scanhead. This lower section is connected to an upper section 83 as shown in FIG. 4 by a cable 90. The upper section 83 includes an LCD display 82 and a battery pack 88. The cable 90 couples video signals from the lower unit 81 to the upper unit for display, and provides power for the lower unit from the battery pack 88. This two part unit is advantageous because the user can maneuver the lower unit and the transducer 84 over the patient in the manner of a conventional scanhead, while holding the upper unit in a convenient stationary position for viewing. By locating the battery pack in the upper unit, the lower unit is lightened and easily maneuverable over the body of the patient.

Other system packaging configurations will be readily apparent. For instance, the front end ASIC 30, the digital signal processing ASIC 40, and the back end ASIC 50 could be located in a common enclosure, with the beamformer of the front end ASIC connectable to different array transducers. This would enable different transducers to be used with the digital beamformer, digital filter, and image processor for different diagnostic imaging procedures. A display could be located in the same enclosure as the three ASICS, or the output of the back end ASIC could be connected to a separate display device. The configuration of FIG. 4 could be changed to relocate the user controls onto the display and battery pack unit, with the ultrasound ASICs located in the unit with the transducer array.

Figure 5:
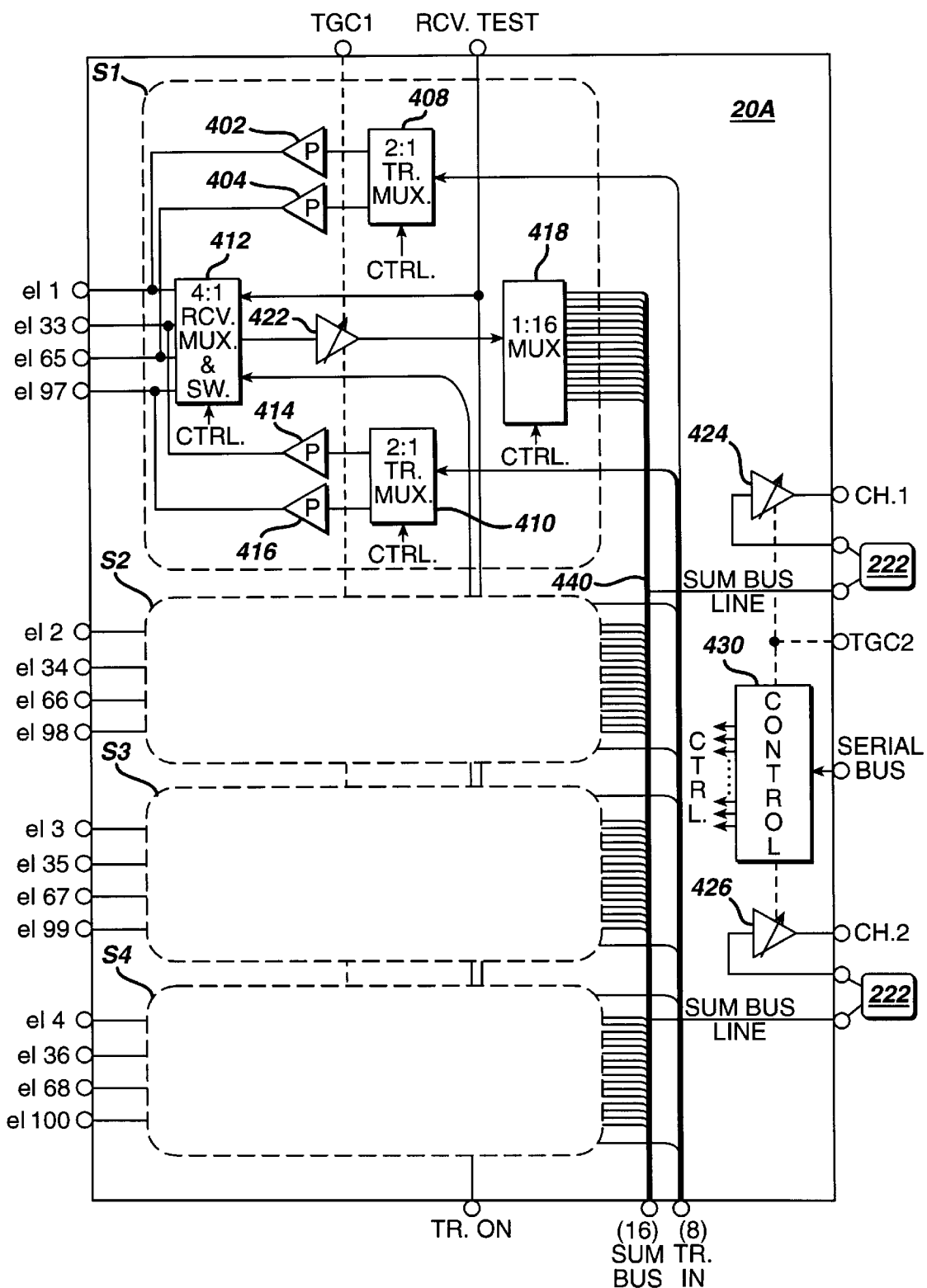
FIG. 5 is a schematic diagram of the transmit/receive ASIC of the ultrasound system of FIG. 1.

Referring now to FIG. 5, a transmit/receive ASIC 20A is shown in greater detail. The signal paths of the ASIC 20A are divided into four identical sections S1, S2, S3, and S4. In this drawing section S1 is shown in internal detail. The section S1 includes two 2:1 transmit multiplexers 408 and 410, each of which is responsive to a pulser signal on one of eight (8) Transmit In lines. Each 2:1 Transmit Multiplexer has two outputs which drive pulsers 402, 404, and 414, 416, the outputs of which are coupled to ASIC pins to which transducer elements are connected. In the illustrated embodiment the 2:1 Transmit Multiplexer 408 is coupled to drive either element 1 or element 65, and the 2:1 Transmit Multiplexer 410 is coupled to drive either element 33 or element 97. The 2:1 Transmit Multiplexers of the other sections of the ASIC are each similarly coupled to four transducer elements. With a separate pulser for each transducer element, the ASIC 20A can independently and simultaneously drive eight of the sixteen transducer elements to which it is connected.

The transducer element pins to which the pulsers of each section are coupled are also coupled to the inputs of a 4:1 Receive Multiplexer and Switch 412. When the pulsers are driving the transducer elements during ultrasound transmission, a signal on a Transmit On line which is coupled to all of the 4:1 Receive Multiplexers and Switches on the ASIC switches them all into a state which presents a high impedance to the high voltage drive pulses, thereby insulating the rest of the receive signal paths from these high voltage pulses. All of the 4:1 Receive Multiplexers and Switches of the ASIC are also coupled to a Receive Test pin of the ASIC, by which a test signal can be injected into the receive signal paths and propagate through the receiver system. During echo reception each 4:1 Receive Multiplexer and Switch couples the signals of one of the four transducer elements to which it is coupled to a 1:16 Multiplexer 418 by way of a first TGC stage 416. The gain of the first TGC stages on the ASIC is controlled by a voltage applied to a TGC1 pin of the ASIC which, in a constructed embodiment, comprises two pins for application of a differential control voltage. The 1:16 Multiplexers of each section of the ASIC each route received echo signals to one of the sixteen (16) lines of a Sum Bus 440. Two of the sixteen Sum Bus lines are shown at the right side of the drawing, and are coupled to filter circuits 222. The filtered bus signals are coupled to input pins leading to two second TGC stages 424 and 426, the gain of which is controlled by the voltage applied to one or two TGC2 pins. The outputs of these second TGC stages in the illustrated embodiment are connected to output pins leading to channels of the ultrasound system's beamformer.

The ASIC 20A also includes a control register 430 which receives control signals over a serial bus from the beamformer. The control register distributes control signals to all of the multiplexers of the ASIC as shown by the Ctrl. input arrows.

A constructed embodiment of ASIC 20A will have a number of pins for supply and bias voltages and ground connections and are not shown in the drawing.

Figure 7:
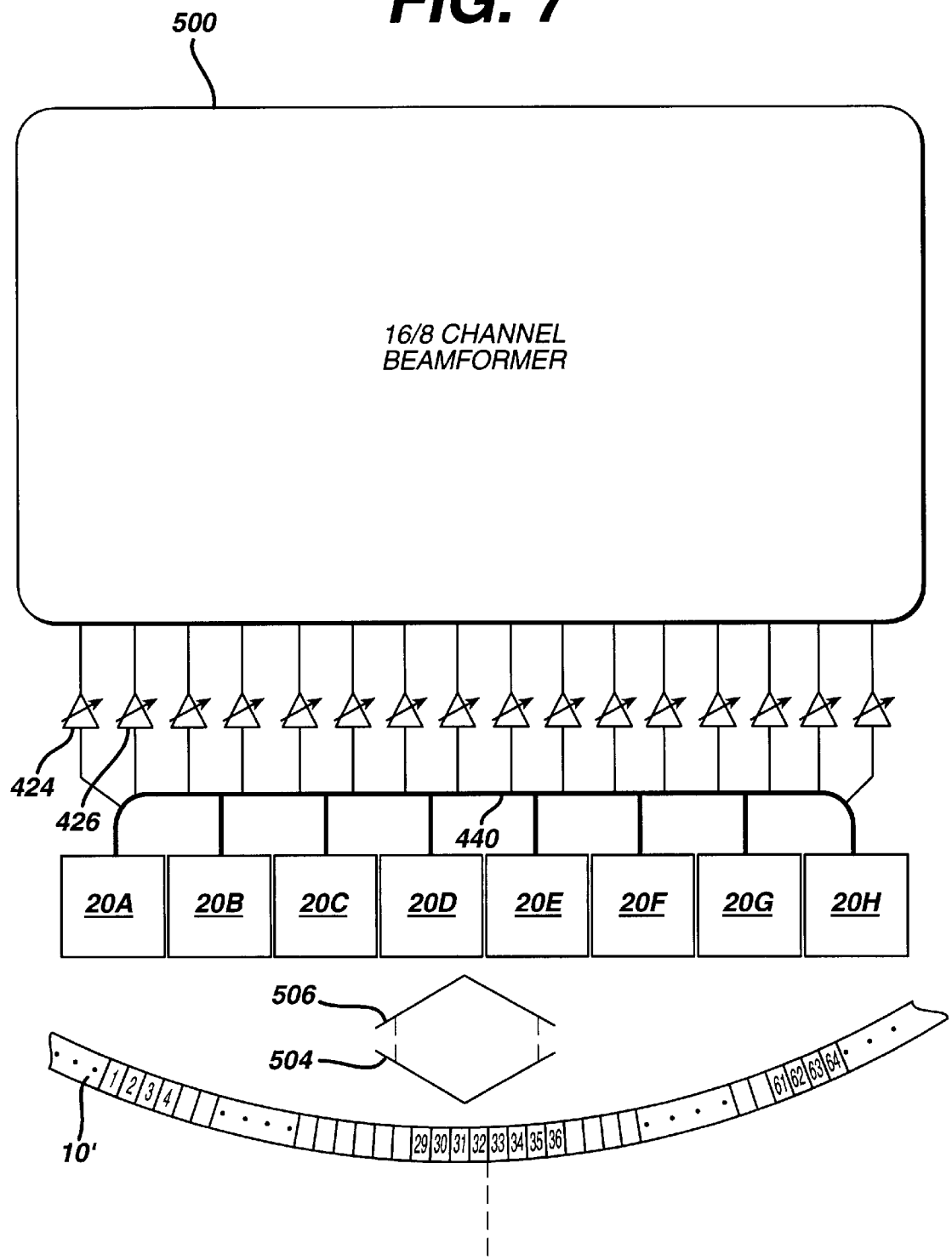
FIG. 7 illustrates the aperture control afforded by the transmit/receive and front end ASICs.

A system using the ASICs of the present invention exhibits an N:1,1:M architecture, where N is the number of transducer elements divided by the maximum aperture size, and M is the number of beamformer channels. These ASICs can be used to connect a wide variety of transducer arrays of various numbers of elements to beamformers of different numbers of channels in numerous ways. An example of this versatility is shown in the system of FIG. 7, which shows a transducer 10' coupled (as indicated by arrows 506,504) to eight transmit/receive ASICs 20A–20H, the Sum Bus 440 of which is coupled by the sixteen second TGC stages of the ASICs to a sixteen channel beamformer 500. (For clarity of illustration the second TGC stages are separately illustrated, although they are in fact integrated on the ASICs.) In this example the eight transmit/receive ASICs, each having sixteen pins for connection to transducer elements, are connected to separately drive all 128 elements of transducer array 10'. The 2:1 Transmit Multiplexers of the eight ASICs are capable of driving 64 elements at once, and thus can operate the transducer array to have a 64 element transmit aperture, represented by transducer element 1–4 . . . 29–36 . . . 61–64 in the drawing. This 64 element aperture is centered between elements 32 and 33. This arrangement is capable of driving all of the elements of a 64 element aperture for each transmitted ultrasound wave. The control registers of the eight ASICs 20A–20H can be conveniently coupled to separate lines of an eight line data bus from the beamformer, each line serving as a serial bus for a particular control register, thereby enabling all eight control registers to be loaded simultaneously.

Echo signal reception over the full 64 element aperture can be accomplished in several ways. One is to employ a folded and synthetic aperture. After a first wave transmission the echoes on elements 17–32 are received and folded together with the echoes from elements 48–33. That is, one Sum Bus line would have the echoes from elements 17 and 48 multiplexed onto it, another Sum Bus line would have the echoes from elements 18 and 47 multiplexed onto it, and so forth. These sixteen folded signals are appropriately delayed and combined by the beamformer to develop a focused signals. After a second wave transmission the outer elements of the aperture are used for folded reception, delayed, and combined with each other and the first focused signals to complete the aperture.

This N:1,1:M ASIC architecture can be used with an eight channel beamformer 500 in place of the 16 channel beamformer by use of the folded and synthetic aperture techniques, or by use of a coarse aperture reception technique, as described in U.S. Pat. No. 4,542,653. In this technique, adjacent elements which were independently excited during beam transmission are paired during reception by combining their received signals and using the same focusing delay for them. Effectively, this means that the transducer pitch is coarser during reception by a factor of two. While this will raise the level of the grating lobes of the received beam pattern, the combined transmit and receive beam patterns will still be acceptable, and the system will benefit by the higher sensitivity of a larger receive aperture. If the grating lobes should prove objectionable, they can be reduced by using an aperiodic aperture, in which the number of elements combined as groups vary from group to group across the aperture. The aperiodic aperture will effectively blend the grating lobe effects into a uniform image background.

In one such arrangement the signals received by four transducer elements are directed to the same Sum Bus line, by suitably programming the 1:16 Multiplexers, for application to the inputs of each of eight beamformer channels. This allows the received signals from elements 17 and 18 to be combined with the received signals from elements 47 and 48 on the same Sum Bus line, and all four signals coupled to the input of one beamformer channel. Thus, both coarse receive and folded aperture techniques are employed simultaneously. A thirty-two element aperture can be received following a single transmitted wave, or a sixty-four element aperture formed by the synthetic aperture technique with two wave transmissions. If only a fine receive aperture is used, the receive aperture is restricted to thirty-two elements with use of the folded and synthetic aperture techniques, or sixteen elements with the folded or synthetic aperture techniques alone.

Thus it is seen that, in the illustrated embodiments, the transmit/receive ASIC 20A operates with sixteen transducer elements, and that several of these ASICs can be used with transducer arrays of a greater number of elements. Six of these ASICs can control a 96 element transducer array, for example.

Figure 6:
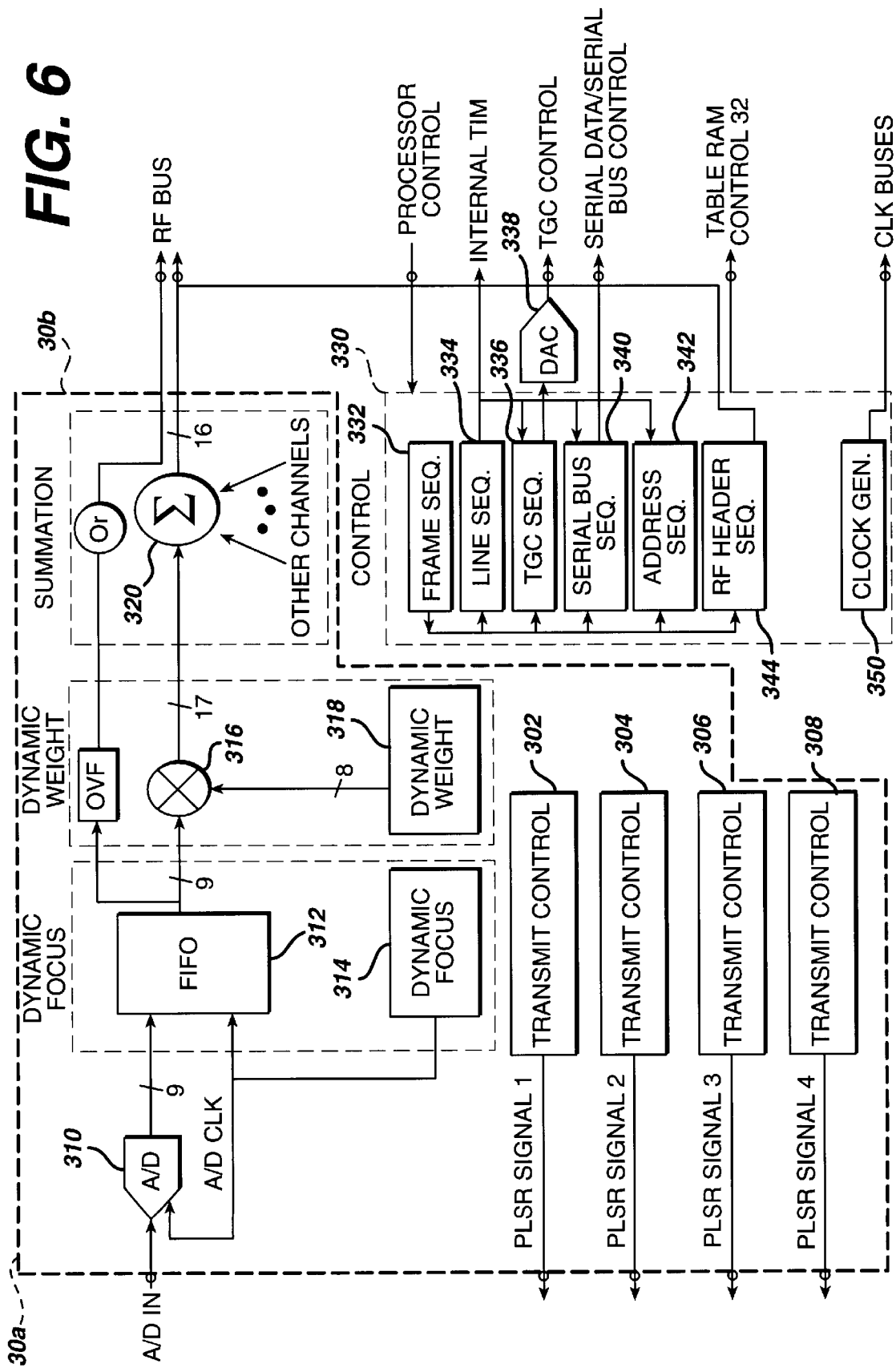
FIG. 6 is a block diagram of the front end ASIC of the ultrasound system of FIG. 1.

A block diagram of the front end ASIC 30 is shown in FIG. 6. This drawing shows one section 30a of the front end ASIC 30. There are eight such sections on the front end ASIC to provide beamforming of the signals of the eight Sum Bus lines from the transmit/receive ASIC 20. Each echo signal output is coupled to the input of an A/D converter 310, where the echo signals are converted to digital data. The A/D converters are located on the same integrated circuit as the beamformer itself, which minimizes the external connection pins of the integrated circuit. Only one analog input pin is required for each beamformer channel, and only one set of digital output pins is required for the coherently summed output signal. The digital data from the A/D converter for each element (or each pair or group of elements in a folded or coarse aperture) is shifted into a first in, first out (FIFO) register 312 by a clock signal A/D CLK. The A/D CLK signal is provided by a dynamic focus controller 314 which defers the start of the clock signal to provide an initial delay, then controls the signal sampling times to provide dynamic focusing of the received echo signals. The length of the FIFO register 312 is determined by the transducer center frequency, the aperture size, the curvature of the array, and the beam steering requirement. A higher center frequency and a curved array will reduce the steering delay requirement and hence the length of the FIFO register, for instance. The delayed echo signals from the FIFO register 312 are coupled to a multiplier 316 where the echo signals are weighted by dynamic weight values provided by a dynamic weight controller 318. The dynamic weight values weight the echo signals in consideration of the effects of the number of active elements, the position of an element in the aperture, and the desired apodization function, as the aperture expands by the inclusion of additional outer elements as echoes are received from increasing depths along the scanline. The delayed and weighted echo signals are then summed with appropriately delayed and weighted echo signals from other elements and echo signals from any other delay stages which are coupled in cascade through a summer 320. The beamformed echo signals, together with synchronous overflow bits, are produced as output scanline data on an RF data bus. Accompanying each sequence of scanline echo signals is identifying information provided by an RF header sequencer on the ASIC, which identifies the type of scanline data being produced. The RF header can identify the scanline as B mode echo data or Doppler data, for instance.

Other digital and sampled data storage devices can be used to provide the beamformer delays, if desired. A dual ported random access memory can be used to store the received digital echo samples, which are then read out from the memory at times or sequences which provide the desired delay for the signals from the transducer elements.

Each section 30a of the front end ASIC includes transmit control circuits 302–308 for four transducer elements of the array. The eight sections thus provide transmit control for 32 elements of the array at the same time, thereby determining the maximum transmit aperture. The transmit control circuits produce waveforms of predetermined durations and periodicities which activate the pulsers at the appropriate times to produce a transmitted acoustic signal which is focused at the desired depth of focus. When only a single front end ASIC with thirty-two transmit control circuits is used with eight transmit/receive ASICS 20A–20H having a total of sixty-four Transmit In lines, as shown in FIG. 7, each transmit control circuit is coupled to the two inputs of each pair of Transmit Multiplexers 408,410 and one of the Transmit Multiplexers is programmed to be enabled and the other disabled for each transmitted wave through the control signals of the control register 430. This effectively converts each pair of 2:1 Transmit Multiplexers to operation as a 4:1 Transmit Multiplexer, giving a maximum transmit aperture of thirty-two independently controlled elements.

The front end ASIC 30 includes a common control section 330 which provides overall control for the transmission and receive functions of the eight beamformer channels on the ASIC. The control section 330 is controlled by and receives data under control of the RISC processor located on the back end ASIC 50. The data tables for a particular image frame are stored in random access memory (RAM) 32 and are loaded into the control section 330 under command of the RISC processor. The control section 330 includes a number of sequencers for the transmit and receive functions. The frame sequencer 332 produces information used by other sequencers which identifies the type of image frame which is to be produced. The frame sequencer may, for example, be loaded with data that defines the next frame as B mode scanlines interspersed between groups of four Doppler scanlines, and that the sequence of scanlines will be all odd numbered scanlines followed by all even numbered scanlines. This information is supplied to the line sequencer 334, which controls the timing required to acquire the desired scanlines. During the scanline acquisition the line sequencer controls the TGC sequencer 336 so that it will produce the desired sequence of TGC control data. The TGC control data from the TGC sequencer is converted to a voltage signal by a digital to analog converter (DAC) 338 and applied to the TGC control input terminal(s) of the transmit/receive ASIC 20. The address sequencer 342 controls the loading of data for a new scanline into various realtime registers of the beamformer such as the registers of the TGC sequencer, the dynamic focus and dynamic weight controllers, and the serial bus sequencer 340, which produces serial data on a serial bus for the control registers of the transmit/receive ASICs of the system. All registers on the front end ASIC which perform real time functions are double buffered. The registers of the transmit/receive ASIC are also double buffered so that the control data can be put on the serial bus and loaded into the various registers during the line preceding the scanline for which the control data is used.

The front end ASIC includes in its control section a clock generator 350 which produces a plurality of synchronous clock signals from which all operations of the system are synchronized. To prevent interference and crosstalk among the closely spaced devices of the system, the video output signal frequency is synchronized to a clock signal of the clock generator, so harmonics of one frequency will not produce interfering components in the other. A crystal oscillator (not shown) is coupled to the front end ASIC 30 to provide a basic high frequency such as 60 MHz from which all of the clock signals of the system may be derived.

Figure 8:
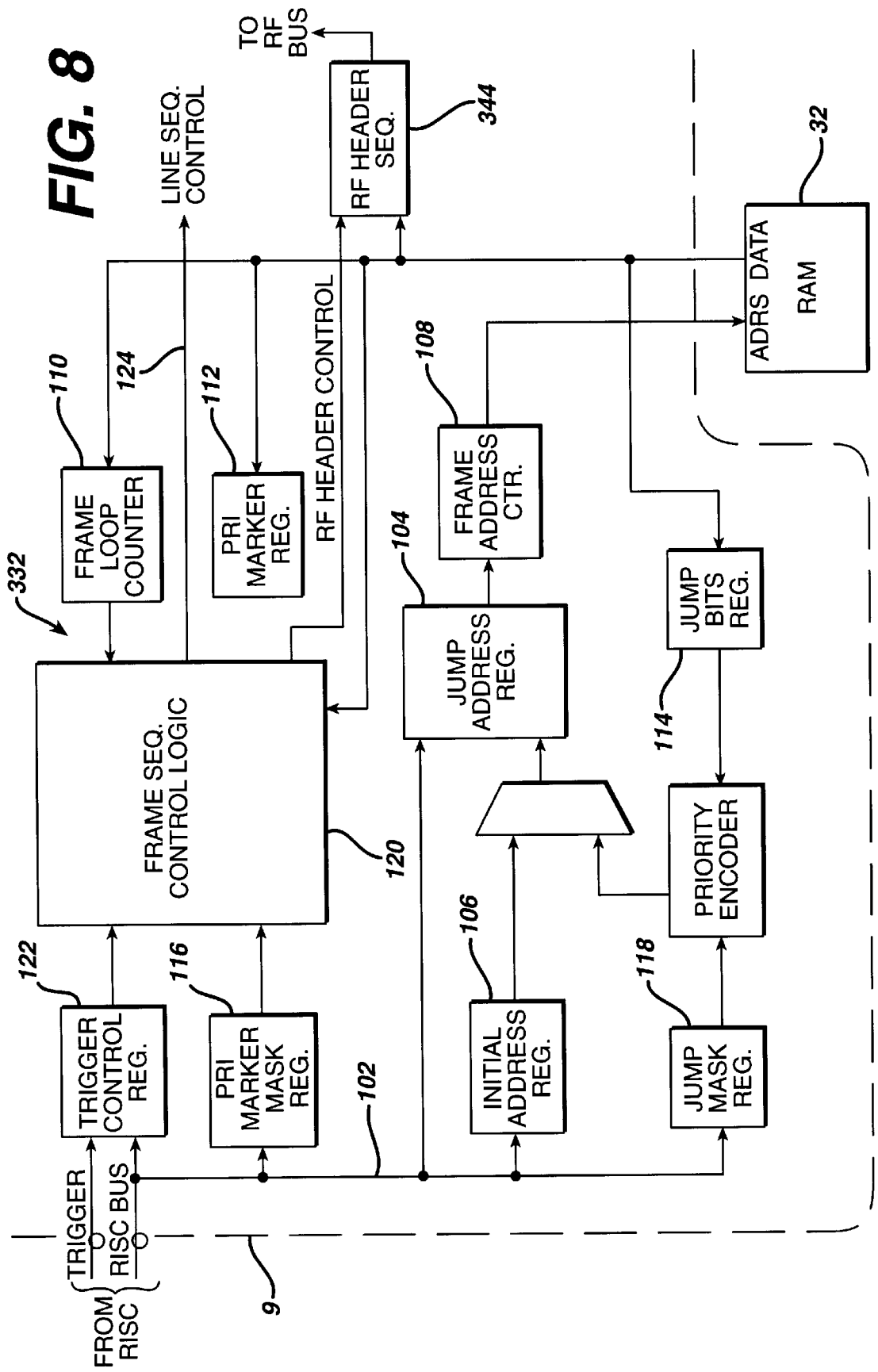
FIG. 8 is a block diagram of the frame and RF header sequencers of the front end ASIC of FIG. 6.

FIG. 8 is a block diagram of the frame and RF header sequencers of the front end ASIC of FIG. 6. In this drawing and the succeeding drawings, broken lines 9 denote the boundary of the ASIC, with the circles on the broken lines indicating terminals (pins) of the ASIC.

Each image frame comprises a group of PRIs, where each PRI includes the transmission of an ultrasound wave and the reception of echoes from the body in response to the wave. Acquisition of an image frame or other sequence such as spectral Doppler is initiated by the receipt of data and commands from the RISC processor on RISC bus 102. A number of RAM addresses called "jump addresses" are stored in jump address register 104. Each jump address is the starting address of a block of data in RAM 32 which is used for a specific scanning procedure. The jump addresses in the register 104 may be updated if desired with new jump addresses provided by the RISC processor. A starting address for the scanning procedure is loaded into the initial address register 106, which selects one of the addresses of register 104 to be loaded into a frame address counter 108. The frame address counter 108 sequentially reads a block of frame control data from the RAM 32 beginning with the address provided by the jump address register 104.

The frame control data comprises five control words which set up the beamformer for the frame data which is to be produced and what is to be done at the end of its production, plus a variable number of RF header data words. The frame data of the frame sequencer conditions other sequencer for the production of the next PRI, where a single PRI is the full cycle of transmission of an ultrasonic wave by the transducer array and reception and beamforming of the echoes resulting from the transmitted wave. The five control words and their data fields are:

| L-SYNAP | T-DTYPE | RF-MODE | PRI-MARKERS |
|---------|---------|---------|-------------|

The L-SYNAP data determines whether a synthetic aperture is to be used. The T-DTYPE data conditions the system for TGC control. The RF-MODE data specifies the number of RF headers to follow for the initial PRI sequence. The PRI-MARKERS data identify the PRI boundaries, and is loaded into the PRI marker register 112.

| FTRIGGER | SUMENA | SOSEL | FLOOP |
|----------|--------|-------|-------|

The FTRIGGER data conditions the system for a test and calibration process. The SUMENA data determines whether echo data from another beamformer ASIC is to be summed with that of the ASIC. The SOSEL data determines whether an internal or external signal is to shift out delayed echo data for summation. The FLOOP data specifies the number of times to repeat the current PRI, and is loaded into the frame loop counter 110.

| L-DTYPE | L-HOLDOFF |
|---------|-----------|

The L-DTYPE data determines the type of ultrasound data to be produced by the PRI, such as 2D echo data or Doppler data. The L-HOLDOFF data determines any delay time to be incurred before the start of the PRI.

| A-MODE | A-MSEL | A-ZONE | A-RAY |
|--------|--------|--------|-------|

The A-MODE data specifies the starting address of a block of data to be used by the address sequencer. The A-MSEL data determines whether the scanline direction is to be determined by an M-line register of the address sequencer, or by the A-RAY field data. The A-ZONE data determines the transmit focal zone. The A-RAY data defines the direction of the ray (scanline) relative to the transducer aperture when specified by A-MSEL.

| JUMP-BITS |
|-----------|

The JUMP-BITS data, in conjunction with the bits of the jump mask register 118, determine the starting address of the next block of frame control data in the RAM 32, and is loaded into the jump bits register 114.

A variable number of RF header data words are next read from the RAM 32 and loaded into the RF header sequencer 344. As explained above, the RF header data is put onto the RF output bus by the sequencer 344 preceding PRI data to notify subsequent processors of the type of PRI data which they are receiving.

After all of these data words have been read, the frame sequencer control logic checks to see whether the RISC processor has issued a stop command. If there is no stop command, the frame sequencer control logic 120 starts the line sequencer by way of the line sequencer control bus 124.

The RISC processor uses several other registers of the frame sequencer of FIG. 8 to exert realtime control over the operation of the beamformer. For instance, the processor can load PRI marker mask data into the PRI marker mask register 116. When the PRI boundary denoted by this mask data matches the PRI boundary of the PRI marker register, as recognized by the frame sequencer control logic, the beamformer will respond to or ignore the match, as determined by the mask data, to execute a realtime function such as updating the TGC function. The RISC processor can load jump mask data into jump mask register 118 which select bits of the jump bits in the jump bits register 114 to direct the next PRI to a particular block data starting address in the jump address register 104. The RISC processor can load realtime commands into the trigger control register 122 which, when triggered by a trigger pulse, are issued to the frame sequence control logic to implement commands such as stop, start, stop on a boundary, reset, M-mode update, or TGC update.

Once the line sequencer has been started, the frame sequencer monitors the realtime command register 122 for commands from the RISC processor and awaits receipt of an end-of-line (EOL) signal from the line sequencer, which causes to frame sequencer to retrieve the frame control data for the next PRI or to terminate acquisition.

Figure 9:
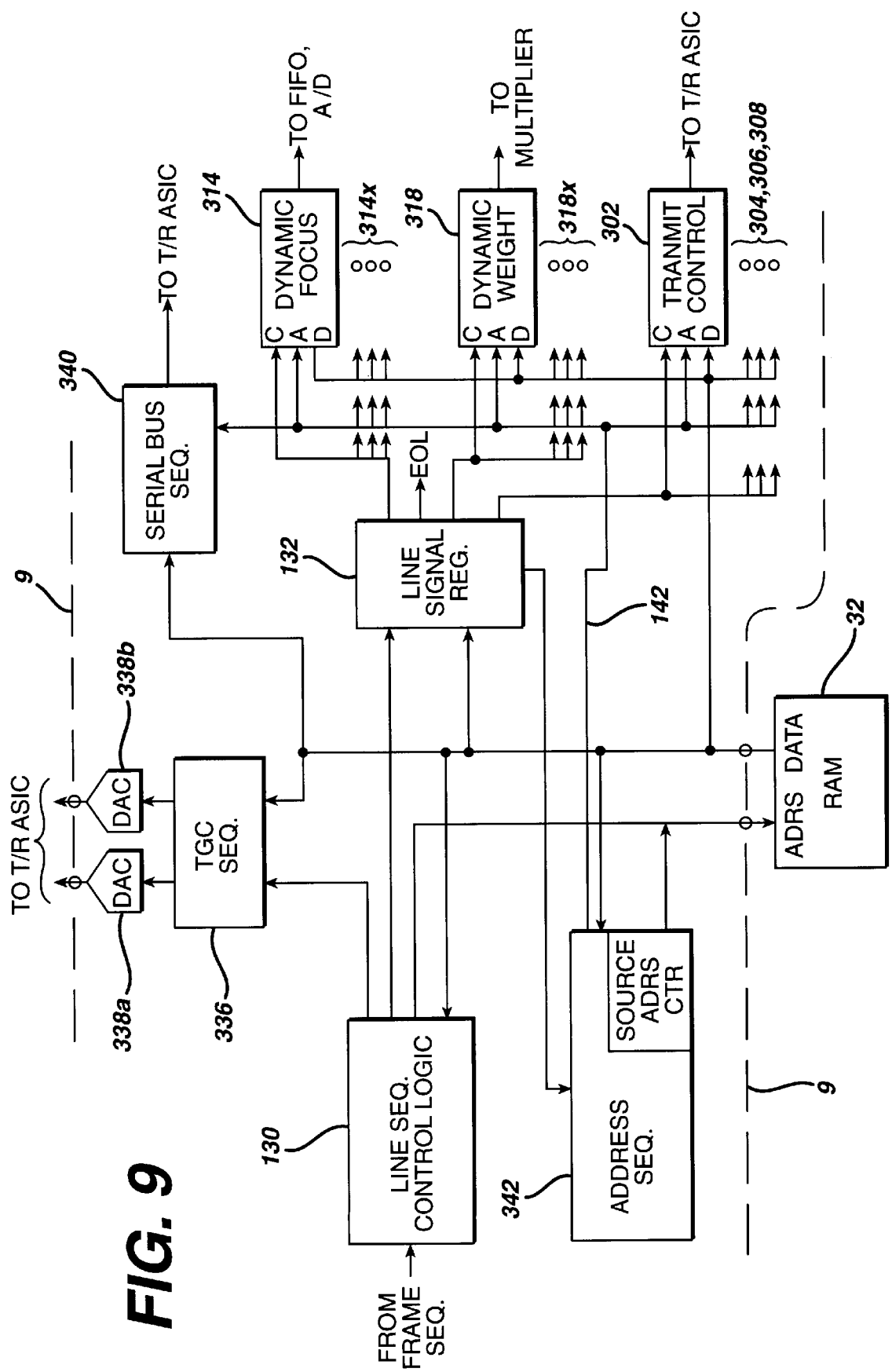
FIG. 9 is a block diagram of the line, TGC, serial bus and address sequencers of the front end ASIC of FIG. 6.

The line, TGC, address, and serial bus sequencer operation is shown in FIG. 9. The line sequencer 334 has two major elements, line sequencer control logic 130 and line signal register 132. The purpose of the line sequencer is to generate the signals that are used to control the overall timing of the PRI. At the start of its operation, the line sequencer reads an RF signal delay word which controls the delay of the RF bus qualifier signals relative to the line sequencer control signals RFDVALN and RFZVALN. The line sequencer then waits for any delay period commanded by the L-HOLDOFF data. Following the delay period the line sequencer control logic 130 begins a repetitive cycle of RAM data accesses for the line signal register, the TGC sequencer, and the address sequencer. The intervals of the cycle are shown in FIG. 9a. The L's at the beginning of the cycle mark intervals during which the line sequencer control logic reads two control data words from RAM 32. The first word is line signal word 0 which is stored in the line signal register 32. The line signal word 0 contains signals that govern the timing of the PRI. An example of the bit designations of the line signal word 0 is shown in Table 1 below. Following the line signal word 0 at the next memory address is line signal word 1, which contains a control signal LSIGDUR that determines the time interval until the next updating of the line signal words.

After the line signal register has been loaded the TGC-SQEN signal of the line signal word 0 enables the TGC sequencer 336. During the W interval of FIG. 9a, the TGC sequencer provides the RISC processor with the opportunity to write a new TGC curve entry into the external RAM 32. This feature allows the modification of the TGC curves during active scanning. The first half of a TGC gain control word defines the gain of the first TGC stages of the transmit/receive ASICs, and the second half of the TGC gain control word defines the gain of the second TGC stages. During the T interval of FIG. 9a the TGC sequencer writes the gain control word to the two digital to analog converters 338a and 338b, which then generate the commanded control voltages for the two banks of TGC amplifiers on the transmit/receive ASIC.

TABLE 1

| Bits | Name | Function |
| --- | --- | --- |
| 0 | PRIRSTN | PRI reset |
| 1 | RDEN | Receive delay enable |
| 2 | SOEN | Shift out enable |
| 3 | TDEN | Transmit delay enable |
| 4 | TGCRSTN | TGC reset |
| 5 | SERLD | Serial bus load |
| 6 | RFDEN | RD data enable |
| 7 | RFDVALN | RF data valid |
| 8 | RFZVALN | RF zone valid |
| 9 | EOLN | End of line |
| 10 | ADDSQEN | Address sequencer enable |
| 11 | TGCSQEN | TGC sequencer enable |
| 12 | LSEQPIN1 | Line sequencer pin 1 |
| 13 | LSEQPIN2 | Line sequencer pin 2 |
| 14 | TX_ON | Trans./rec. switch control |
| 15 | — | unused |

The serial bus sequencer 340 is loaded with control data from the external RAM 32 under control of the address sequencer 342. The serial bus sequencer performs a parallel to serial conversion of the control data and transmits the result in serial form to the holding registers of the transmit/receive ASIC's double buffered registers. The SERLD signal from the line signal word 0 is also provided to the transmit/receive ASIC and is used to cause the transfer of information from the holding registers to the working registers on the transmit/receive ASIC.

The ADDSQEN signal commands the address sequencer 342 to load new control data into the realtime registers on the front end ASIC during the address sequencer intervals A of FIG. 9a, which comprise most of the time of the sequencers of FIG. 9. The address sequencer does this by addressing the registers over an internal address bus 142 while using a source address counter 144 to address a sequence of data entries in the RAM 32. The data in the addressed RAM locations is then loaded into the addressed registers such as the dynamic focus registers 314, 314x, the dynamic weight registers 318, 318x, and the transmit control registers 302, 304, 306, 308, and so forth. In this way the internal registers on the beamformer ASIC are conditioned to transmit and receive the next PRI.

The PRIRSTN signal is a time marker from which the events of transmission and reception are marked. The TDEN signal, together with the transmit delay and waveform data stored in registers of the transmit control circuits, govern the activation of the transmit control circuits to transmit the desired focused ultrasound beam.

The contents of the line signal register are periodically updated during the PRI at the intervals determined by the control signal LSIGDUR. At the end of the PRI the line signal word 0 in the line signal register 132 issues an end of line signal EOLN to the frame sequencer to mark the end of the current PRI, which returns control of the beamformer to the frame sequencer for the next PRI. The sequencers continue to operate in this manner until a full frame of image data (in the case of an imaging operation) has been acquired.

Figure 10:
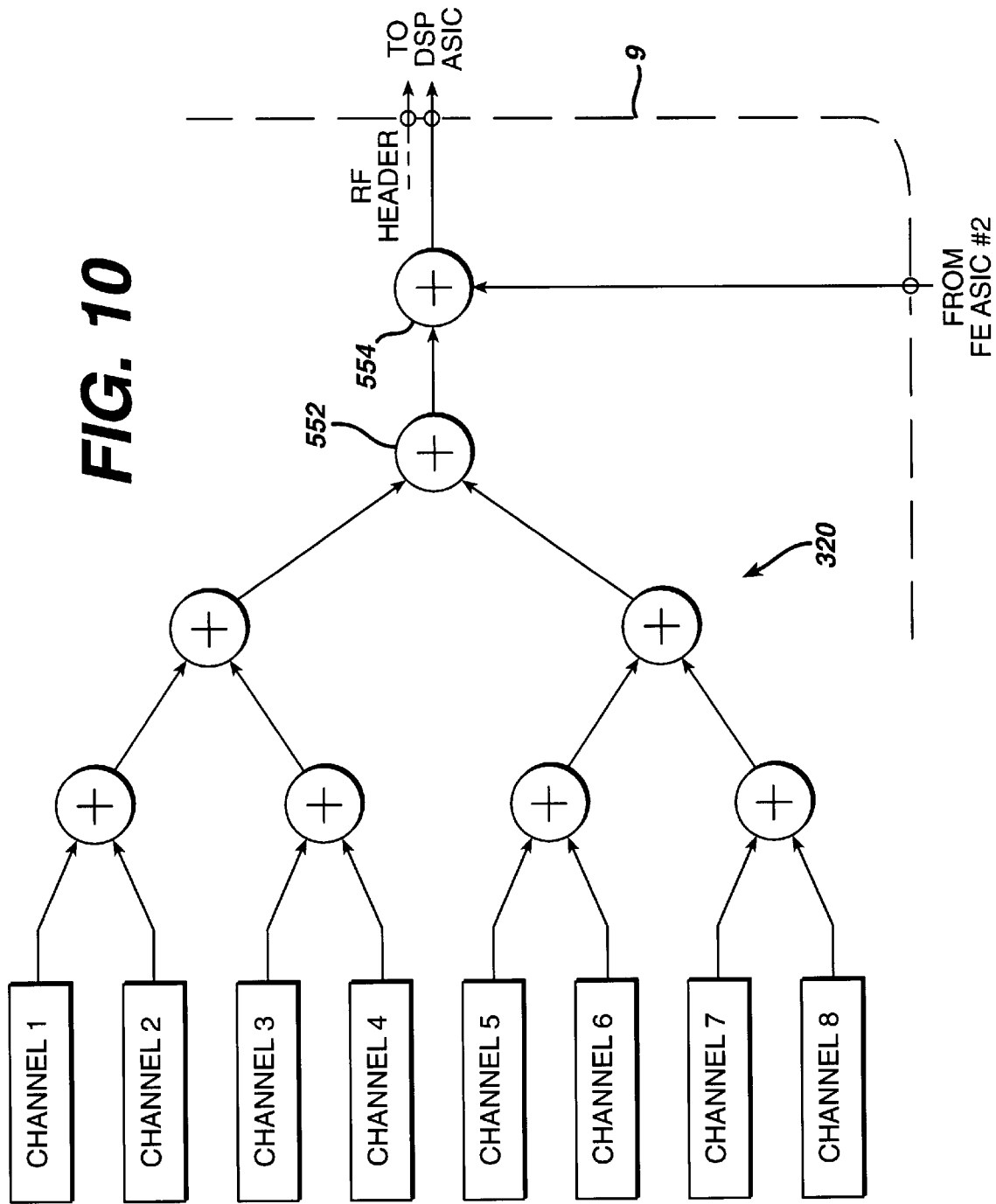
FIG. 10 is a block diagram of the summing network for the beamformer channels of the front end ASIC of FIG. 6.

FIG. 10 illustrates the summing network 320 which combines the delayed echo values from the eight channels on the front end ASIC to form a coherent echo sample. A network of summers add all of the delayed echoes on the ASIC at the output of summer 552. This summer is succeeded by another summer 554, which adds in the summed echoes from another beamformer ASIC. This additional summer 554 permits a number of front end ASICs to be cascaded to form a beamformer with a larger number of channels, such as a sixteen or thirty-two channel beamformer. Eight of the ASICS 30 can be cascaded to form a sixty-four channel beamformer, for example.

Figure 11:
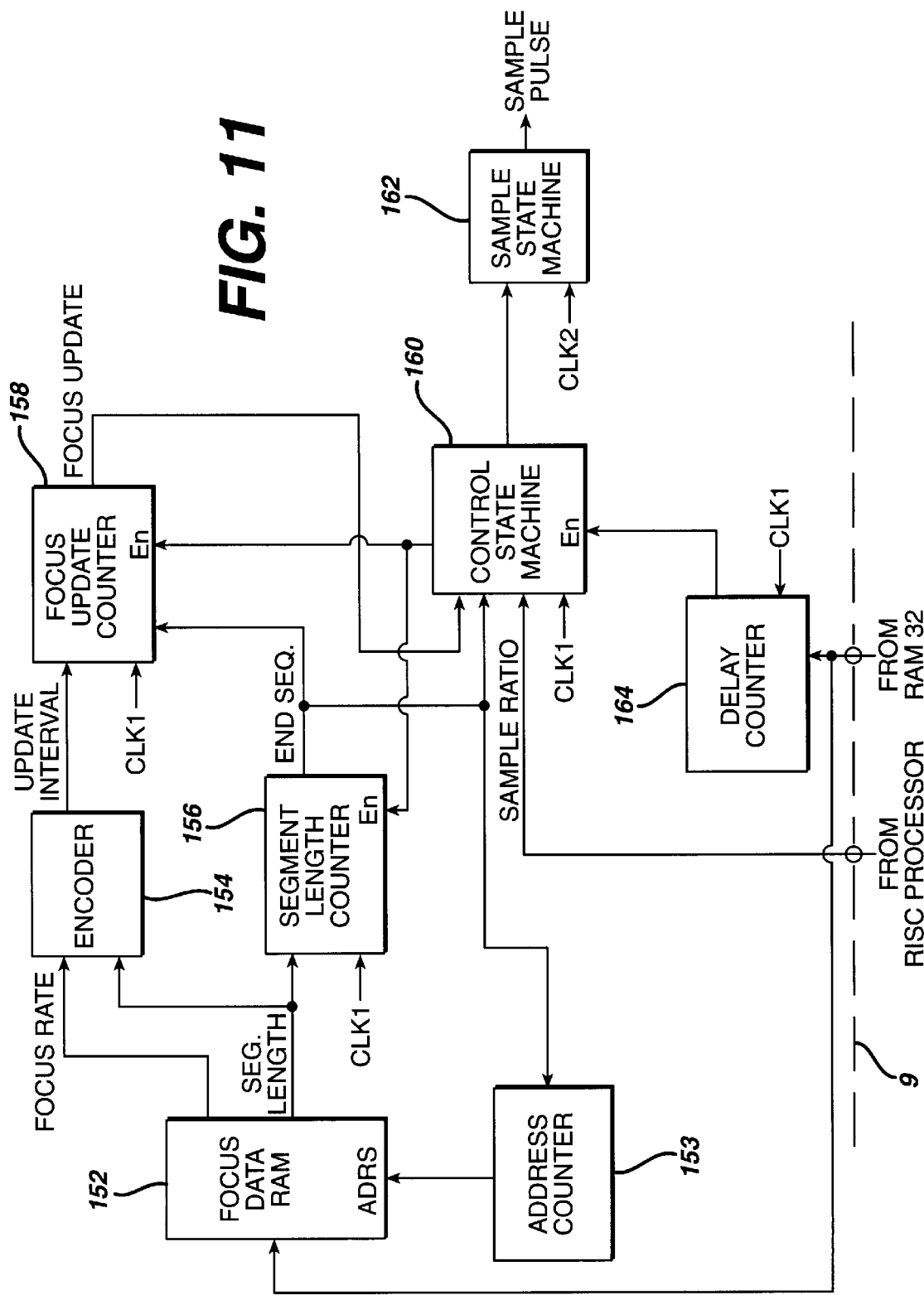
FIG. 11 is a block diagram of one of the dynamic focus controllers of the front end ASIC of FIG. 6.
Figure 13:
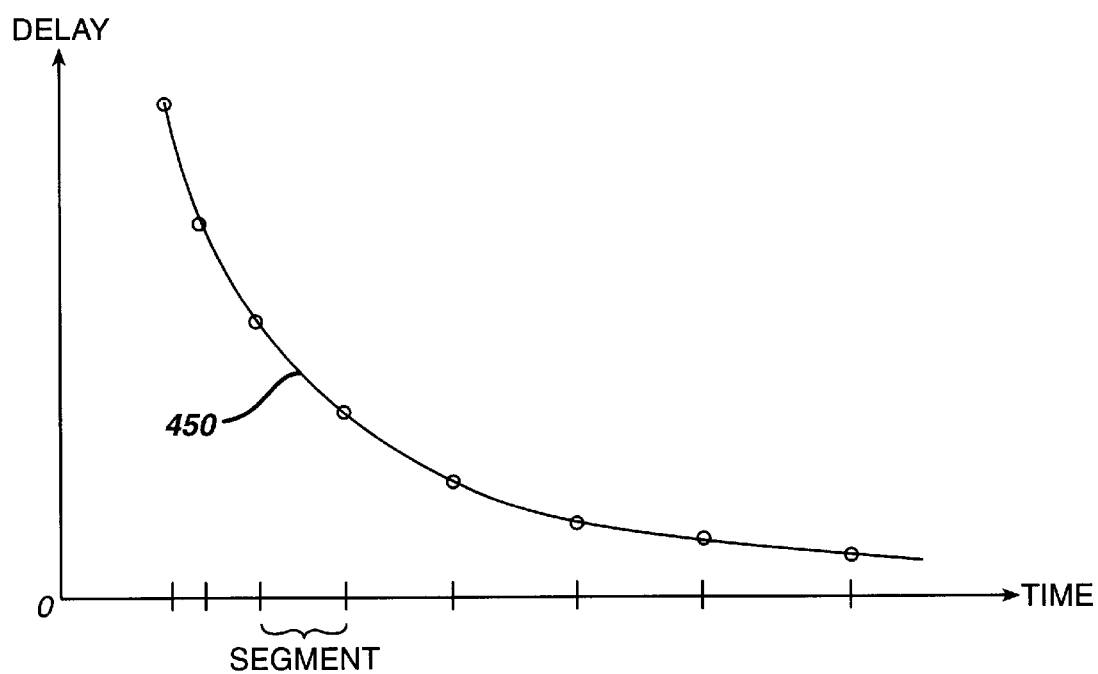
FIG. 13 is an exemplary focus control curve used to explain the dynamic focus controller of FIG. 11.

FIG. 11 illustrates the operation of one of the dynamic focus controllers 314 of the front end ASIC. The dynamic focus controllers control the time delays of the digital delays 312 in accordance with the well-known exponential equation for dynamic focus delay variation, which is shown graphically in FIG. 13. As curve 150 illustrates, the delay of each digital delay starts at a relatively high level, then decrease with time. The exponential curve 150 is divided by circles into a number of segments, as shown along the abscissa of FIG. 13, during which the focus is changed. As the curve and segments indicate, the rate of focus change declines with time as echoes are received from increasing distances.

The arrangement of FIG. 11 implements this function by loading two values stored in an internal focus data RAM 152 into an encoder and a counter of the dynamic focus controller. One of these values defines the length of a focal curve segment, and is loaded into both the encoder 154 and the segment length counter 156. The second value defines the focus rate, the number of focal updates during the segment, and is loaded into the encoder 154. The encoder uses the two values supplied by the internal RAM 152 to produce an update interval value, the interval of time between focus updates. The update interval value is repetitively counted down by the focus update counter, and at the terminal count of the counter a focus update signal is produced, triggering a command to control state machine 160 to update the focus. The control state machine 160 then issues a command to the sample state machine to adjust the phase of the sampling interval, and the sample state machine 162 then issues a sample pulse with the desired phase relation to a clock signal CLK2.

As sampling pulses are being produced during the current focus segment (see FIG. 13), the segment length counter 156 is counting the duration of the segment. When the segment length counter reaches the end of the segment, it issues an end segment signal to the focus update counter to load the next update interval into the counter 158. The control state machine 160 is informed of the end of the segment, as is an address counter 153, which increments its count to address the next location of the focus data RAM 152 to produce the values for the next focal segment.

Also factored into the sampling pulse rate by the control state machine 160 is the sampling ratio provided by the RISC processor, which is a code which indicates the ratio of the master clock frequency of the system to the nominal sample frequency.

The dynamic focus controller is inhibited by a signal on the enable input of the control state machine 160 for an initial delay period at the start of the PRI that is counted by a delay counter 164. After the counter 164 has counted this initial delay, the control state machine 160 is enabled, which in turn enables the segment length counter 156 and the focus update counter 158 to begin their operation for the current PRI.

Figure 12:
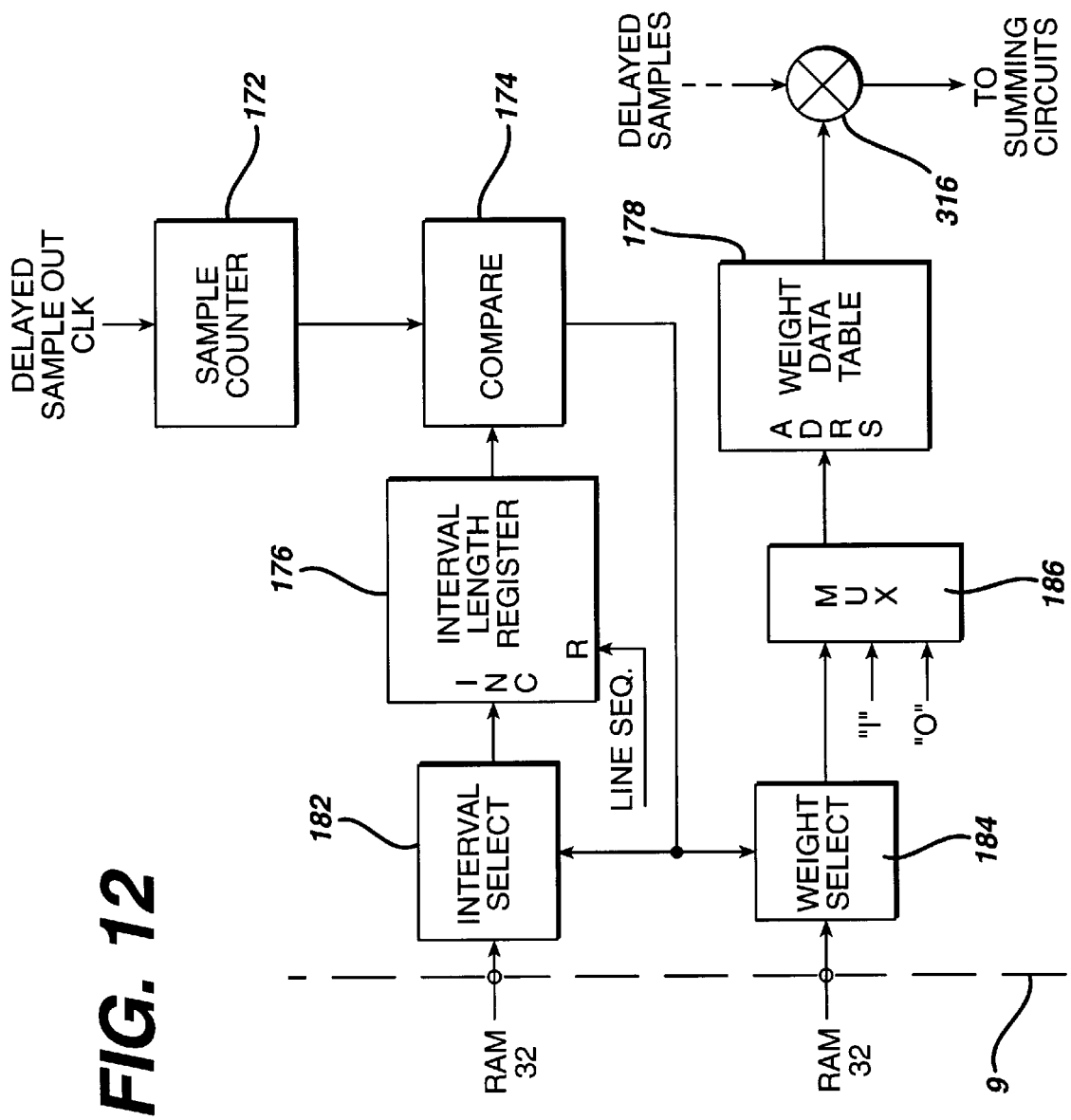
FIG. 12 is a block diagram of one of the dynamic weight controllers of the front end ASIC of FIG. 6.
Figure 15:
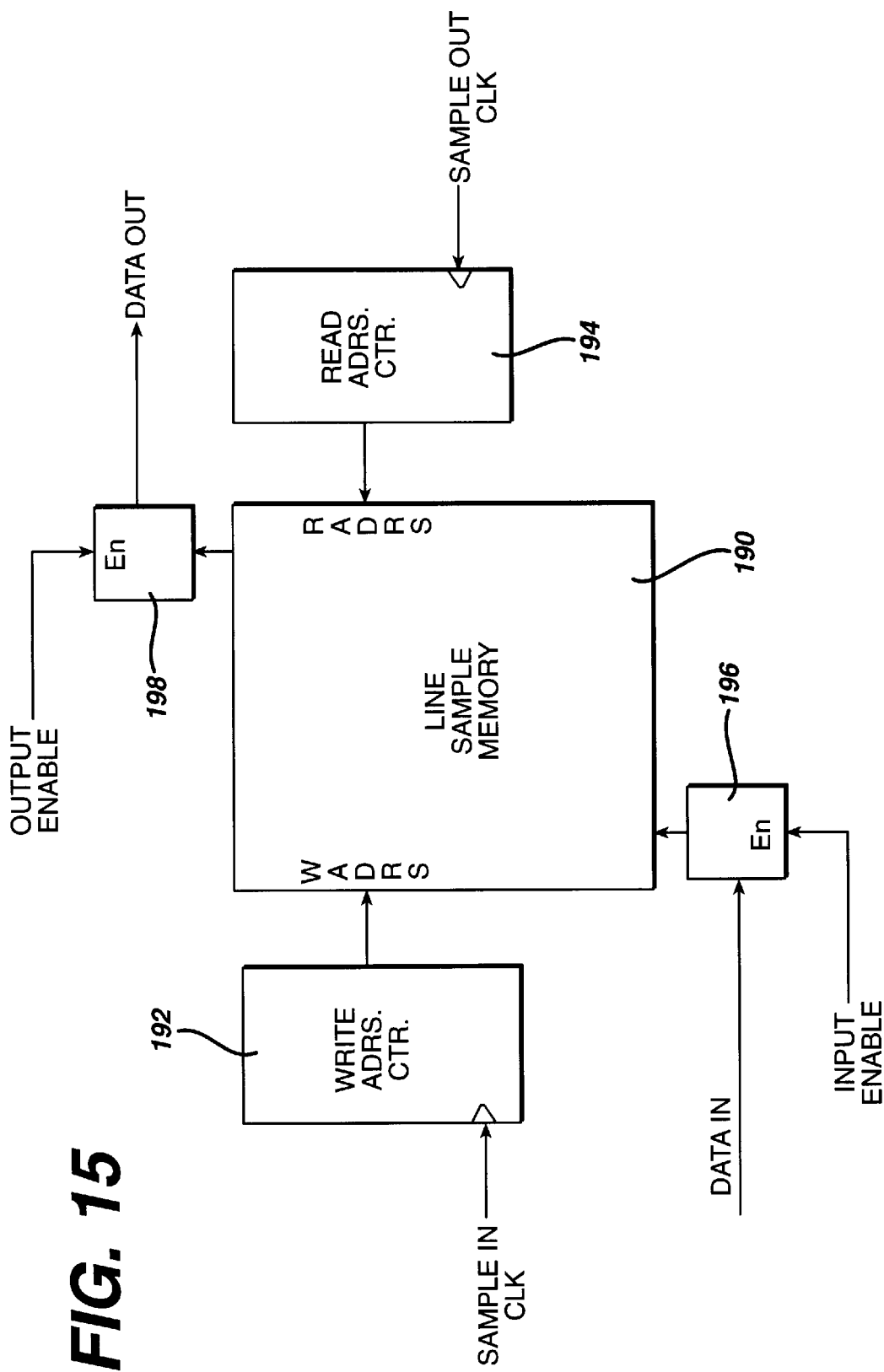
FIG. 15 illustrates a preferred digital delay device for the beamformer of the present invention.

The operation of the dynamic weight controllers 318 is illustrated in FIGS. 12 and 15. The outputting of delayed digital echo signals begins with the setting of the shift out enable signal bit SOEN in line signal word 0. The SOEN signal activates the Read Address counter 194 of the line sample memory 190 in FIG. 15. This drawing illustrates a dual ported RAM used for digital delay 312. In this example the dual ported RAM operates in the manner of a FIFO by the use of sequential addressing for the storage addresses of the received echo signals. Received echoes are written into consecutively addressed locations of the memory 190 by clocking a Write Address Counter 192. Echo signals applied to the Data In input of write amplifiers 196 will be written to the locations addressed by the Write Address Counter 192 when the write amplifiers 196 are enabled by an Input Enable signal. Similarly, and concurrently if desired, stored echo signals can be read from the memory 190 in the order in which they were received by incrementing a Read Address Counter 194 while applying an Output Enable signal to read sense amplifiers 198.

Upon the occurrence of the SOEN signal the Read Address Counter 194 becomes active and is incremented by the Sample Out clock. During the initial output period, termed the "weight delay" period, the Read Address Counter 194 is incremented to the starting address from which data is to be taken for summation. During this weight delay period the Output Enable signal has not activated the sense amplifiers 198 for the memory. Consequently the memory is not outputting echo samples at this time, and power is conserved by the inactive output state of the memory at this time.

When the predetermined weight delay period has ended and the Read Address Counter 194 is pointing to the desired starting address for the sequence of echoes to be summed, the Output Enable signal activates the memory sense amplifiers 198 and echo signals are read from the memory 190 and applied to the multipliers 316. These echo signals are termed "delayed samples" in FIG. 12 by reason of their occurrence following the weight delay period. At the same time, Sample Out clock pulses are applied to a sample counter 172 in FIG. 12. This Sample Out clock is termed Delayed Sample Out clock in FIG. 12, again by reason of its occurrence following the weight delay period.

The clocking of the output echo samples is counted by the sample counter 172, which counts an interval over which the weighting of the delayed samples is to be held constant. The count of the sample counter 172 is compared with the counts of the current interval which is supplied by an interval length register 176. During the interval a weight data table 178 is producing a weight for the multiplier 316 to weight the samples which are outputted by the memory 190. When the comparator 174 produces a signal indicating the end of the current weighting interval, the signal from the comparator causes the interval select controller 182 and the weight select controller 184 to select a new interval to count and weight to use to weight the echo signals. This causes the delayed samples to be multiplied by a new weight for a new weighting interval.

The interval select controller 182 and the weight select controller 184 are programmable controllers into which new control data may be loaded from the RAM 32. When the comparator 174 produces a signal at the end of the current interval, the interval select controller 182 will either increment the register 176 to a new interval length, or will hold the register 176 at its current output length, depending upon the control data of the interval select controller 182. At the end of the current PRI the line sequencer will reset the interval length register 176 to its starting interval value. The weight select controller 184 operates similarly to selectively increment through a sequence of addresses for a weight select data table 178. When the weight select controller produces a new address, the new address is applied to the weight data table 178, and the weight value of the addressed location in the data table is applied to the multiplier 316 which uses the value to weight the echo samples. The address from the weight select controller 184 is applied by way of a multiplexer 186, which is also used to force the weight data table 178 to produce a weight of "1" or "0" during testing or calibration sequences.

Figure 14:
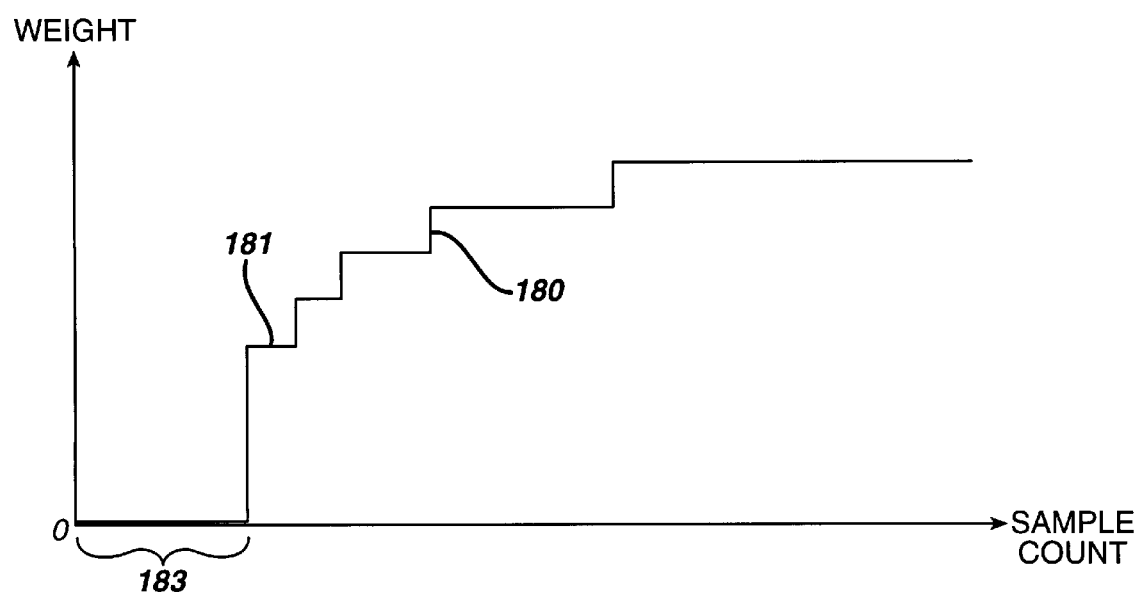
FIG. 14 is an exemplary weighting function curve used to explain the dynamic weight controller of FIG. 12.

An example of the weighting function implemented by the arrangement of FIG. 12 is shown by the curve 180 in FIG. 14. As this curve shows, for the initial weight delay interval 183 no weights are produced by the arrangement, as no echo values are produced from the dual ported RAM memory 190. After this initial interval the curve is incremented to a first level 181 and then on to greater weights as time progresses. Concurrently, the intervals over which the weight does not change, shown by the horizontal step levels on the curve 180, grow increasingly longer. It should be understood that weights of zero can also be used, and their initial use would effectively increase the weight delay interval 183.

The back end ASIC 50 is the location of the RISC processor 502, which is used to coordinate the timing of all of the operations of the handheld ultrasound system. The RISC processor is connected to all other major functional areas of the ASICs to coordinate process timing and to load buffers and registers with the data necessary to perform the type of processing and display desired by the user. Program data for operation of the RISC processor is stored in a program memory 52 which is accessed by the RISC processor. Timing for the RISC processor is provided by clock signals from the clock generator 350 on the front end ASIC 30. The RISC processor also communicates through a PCM-CIA and/or infrared transmitter interface, by which the processor can access additional program data or transmit image information remotely. The interface can connect to a telemetry link or a modem for the transmission of ultrasound images from the handheld unit to a remote location, for instance.

The RISC processor is operated under user control by commands and entries made by the user on the user control 70. A chart showing control functions, the type of controls, and their description is shown in FIG. 16. It will be appreciated that a number of functions, such as patient data entry, Cineloop operation, and 3D review, will operate through menu control to minimize the number of key or button controls on the small handheld unit. To further simplify the unit a number of operating functions are preprogrammed to specific diagnostic applications and will operate automatically when a specific application is selected. Selection of B mode imaging will automatically invoke frequency compounding and depth dependent filtering, for instance, while a four multiplier filter will automatically be set up as a wall filter when Doppler operation is selected. The menu selection of specific clinical applications can automatically invoke specific feature settings such as TGC control characteristics and focal zones, for example.

What is claimed is:

1. A handheld ultrasound device comprising:
an enclosure;
an array transducer located in said enclosure and accessing a patient through an acoustic window;
a receiver, located in said enclosure, for receiving echoes from the elements of said array transducer; and
a digital beamformer, coupled to said receiver, for digitally delaying and combining echo signals received by said elements of said array transducer to form an ultrasonic beam.

2. The handheld ultrasound device of claim 1, wherein said digital beamformer includes a digital delay device for digitally delaying echo signals received from elements of said array transducer.

3. The handheld ultrasound device of claim 2, wherein said digital beamformer includes a plurality of digital delay devices coupled to receive echo signals from different transducer elements, and
wherein said digital delay devices are coupled in cascade to sum delayed echo signals.

4. The handheld ultrasound device of claim 2, wherein said digital delay device comprises a plurality of digital FIFO registers.

5. The handheld ultrasound device of claim 2, wherein said digital delay device comprises a plurality of digital storage devices.

6. The handheld ultrasound device of claim 5, wherein said digital storage devices comprise dual ported random access memories.

7. The handheld ultrasound device of claim 2, wherein the commencement of storage of received echo signals into said digital storage devices is deferred to provide an initial delay.

8. The handheld ultrasound device of claim 1, wherein said digital beamformer includes a dynamic focus controller for providing dynamic focusing of the received echo signals.

9. The handheld ultrasound device of claim 8, further comprising a plurality of analog to digital (A/D) converters for converting received echo signals to digital samples, and wherein said dynamic focus controller (focusing comprises means for controlling the signal sampling times of said A/D converters.

10. The handheld ultrasound device of claim 1, wherein said digital beamformer further includes a weighting circuit for weighting received echo signals as a function of the effects of a dynamic receive aperture.

11. The handheld ultrasound device of claim 10, wherein said digital beamformer includes a plurality of channels, wherein each channel includes a digital delay device, and wherein said weighting circuit comprises a digital multiplier coupled to the output of each digital delay device.

12. The handheld ultrasound device of claim 1, further comprising a plurality of transmit multiplexers coupled to said elements of said array transducer,
wherein said array transducer has a plurality of transmit apertures each formed by a group of adjacent transducer elements,
wherein each element of a group of said adjacent transducer elements is coupled to a different one of said plurality of transmit multiplexers,
whereby said transducers of a group are all excited by means of said plurality of transmit multiplexers during an ultrasonic wave transmission sequence.

13. The handheld ultrasound device of claim 1, further comprising a plurality of receive multiplexers each coupled between a plurality of transducer elements and said beamformer,
wherein said receive multiplexers are responsive to transducer aperture selection signals for coupling echo signals received by selected ones of said transducer elements to said beamformer to be combined in an ultrasound beam.

14. The handheld ultrasound device of claim 13, wherein said array transducer has a plurality of receive apertures each formed by a group of adjacent transducer elements,
wherein each element of a group of said adjacent transducer elements is coupled to a different one of said plurality of receive multiplexers,
whereby echo signals received by the transducers of a group are all coupled by means of said plurality of receive multiplexers to said beamformer during reception of an ultrasonic scanline.

15. The handheld ultrasound device of claim 13, wherein said receive multiplexers are connected to form a folded receive aperture.

16. The handheld ultrasound device of claim 13, further comprising bandpass filter circuitry coupled to filter echo signals received by said elements of said array transducer.

17. A handheld ultrasound device comprising:
an enclosure;
an array transducer located in said enclosure and accessing a patient through an acoustic window;
a transceiver circuit, mounted in said enclosure and connected to the elements of said array transducer, for exciting said elements to transmit ultrasonic waves and receiving echoes from said elements; and
a digital beamformer, coupled to said transceiver circuit, for controlling the transmission of ultrasonic waves by said array transducer and delaying and combining echo signals received by said elements of said array transducer to form an ultrasonic beam.

18. The handheld ultrasound device of claim 17, wherein said array transducer comprises a curved linear array transducer.

19. An integrated circuit for an ultrasonic imaging system comprising:
a plurality of A/D converters located on said integrated circuit;
a plurality of digital delays located on said integrated circuit and coupled to receive digital signals produced by said A/D converters; and
a summing circuit coupled to combine digital signals from said digital delays.

20. The integrated circuit of claim 19, wherein said integrated circuit further includes a plurality of analog input pins coupled to the inputs of said A/D converters, and a plurality of output pins at which digital signals produced by said summing circuit are provided.

21. The integrated circuit of claim 19, wherein said digital delays comprise a plurality of digital delay lines.

22. The integrated circuit of claim 21, wherein said digital delay lines comprise FIFO registers.

23. The integrated circuit of claim 21, wherein said digital delay lines comprise a plurality of random access memories.

24. The integrated circuit of claim 23, wherein said random access memories comprise dual ported RAMS.

25. A handheld ultrasonic imaging device, comprising:
an array transducer; and
a beamforming integrated circuit chip including:
a plurality of A/D converters having inputs coupled to receive signals from said array transducer;
a plurality of digital delays coupled to receive digital signals produced by said A/D converters; and a summing circuit coupled to combine digital signals from said digital delays; and one or more enclosures for housing said array transducer and said integrated circuit.

26. The handheld ultrasonic imaging device of claim 25, further comprising:

a second beamforming integrated circuit chip housed in one of said enclosures and including:
 a plurality of A/D converters having inputs coupled to receive signals from said array transducer;
 a plurality of digital delays coupled to receive digital signals produced by said A/D converters; and
 a summing circuit coupled to combine digital signals from said digital delays; and an interconnection for connecting the summing circuit of said second beamforming integrated circuit chip to the summing circuit of said first named beamforming integrated circuit chip.

27. The handheld ultrasonic imaging device of claim 25, wherein said beamforming integrated circuit chip includes eight A/D converters and eight digital delays fabricated on a unitary integrated circuit chip.

28. The handheld ultrasonic imaging device of claim 25, wherein said beamforming integrated circuit chip includes multiples of eight A/D converters and eight digital delays fabricated on a unitary integrated circuit chip.

* * * * *

UNITED STATES PATENT AND TRADEMARK OFFICE
CERTIFICATE OF CORRECTION

| | |
|---|---|
| PATENT NO. | : 5,817,024 |
| APPLICATION NO. | : 08/863937 |
| DATED | : October 6, 1998 |
| INVENTOR(S) | : William R. Ogle et al. |

It is certified that error appears in the above-identified patent and that said Letters Patent is hereby corrected as shown below:

In the claims:

Claim 1, Column 15, Line 11, after "beam" insert --, wherein said enclosure including said array transducer and said receiver, and said digital beamformer comprise a handheld ultrasound device weighing less than ten pounds.--.

Signed and Sealed this

Second Day of October, 2007

JON W. DUDAS
*Director of the United States Patent and Trademark Office*